United States Patent [19]

Vidaver et al.

[11] Patent Number: 5,014,225
[45] Date of Patent: May 7, 1991

[54] APPARATUS AND METHOD FOR DETERMINING PLANT FLUORESCENCE

[75] Inventors: William Vidaver, West Vancouver; Peter Toivonen, Chilliwack; Sylvain Dube, Vancouver, all of Canada

[73] Assignee: Simon Fraser University, Burnaby, Canada

[21] Appl. No.: 390,905

[22] Filed: Aug. 8, 1989

[30] Foreign Application Priority Data

Aug. 9, 1988 [CA] Canada .................. 574252-8

[51] Int. Cl.⁵ ............................................ G01N 33/48
[52] U.S. Cl. .................................. 364/550; 250/461.2; 73/865.6
[58] Field of Search ............... 364/550, 551.01, 571.01; 356/73, 318, 432; 250/459.1, 461.1, 461.2, 458.1; 47/58; 362/805; 374/142; 73/865.6, 336; 340/600

[56] References Cited

U.S. PATENT DOCUMENTS

| | | | |
|---|---|---|---|
| 4,084,905 | 4/1978 | Schreiber et al. | 356/85 |
| 4,678,330 | 7/1987 | Gutschick et al. | 356/432 X |
| 4,710,033 | 12/1987 | Hirano et al. | 250/458.1 X |
| 4,768,390 | 9/1988 | Baker et al. | 73/336 X |
| 4,768,513 | 9/1988 | Suzuki | 356/318 |
| 4,786,170 | 11/1988 | Groebler | 356/318 |
| 4,804,849 | 2/1989 | Booth et al. | 250/459.1 |
| 4,855,930 | 8/1989 | Chao et al. | 364/554 X |
| 4,877,583 | 10/1989 | Miwa et al. | 250/461.2 X |
| 4,890,247 | 12/1989 | Sarrine et al. | 364/571.04 |

FOREIGN PATENT DOCUMENTS

| | | |
|---|---|---|
| 0209247 | 1/1987 | European Pat. Off. . |
| 3303510 | 7/1983 | Fed. Rep. of Germany . |
| 1590444 | 7/1970 | France . |
| 0489795 | 6/1970 | Switzerland . |
| 1138781 | 2/1967 | United Kingdom . |

OTHER PUBLICATIONS

An Integrated Sphere Leaf Chamber, Idle, D. B. and Proctor, C. W., 1983-1986, pp. 437-439.
An Integrated Sphere for the Rapid Nondestructive . . . Chlorophyll Content, McDowall, F. D. H.—pp. 3072-3079, 1982.
Photosystem II Photosynthetic . . . Fluorescence Induction in Leaves, Malkin, S., Armond, P. A., Mooney, Fork—1981, pp. 570-579.
"Automatic Integrating Fluorometer . . . and Scope-85", Reve. Sci. Instr., Morrissette, Meunier and Popovic—, pp. 934-936, Jun. 1988, vol. 59 (6).

(List continued on next page.)

Primary Examiner—Joseph L. Dixon
Attorney, Agent, or Firm—Shlesinger, Arkwright & Garvey

[57] ABSTRACT

An apparatus and method for determining the photosynthetic activity of a plant by determining the chlorophyll fluorescence of the plant is provided. The apparatus includes a light impermeable housing, a light to illuminate the housing, a light intensity in the housing and to adjust the light intensity controller. The light intensity may be between zero and 700 micromoles of photons per square meter per second. The monitor may be a photodiode protected by light filters which permit only light of wavelengths corresponding to plant fluorescence emission to pass to the photodiode. A computer analysis of the data obtained, corrects for Dark and Straylight signals in the housing and normalizes the data by correcting for the Fo fluorescence. A method of estimating Fo is provided which includes illuminating a light impermeable chamber housing a plant with light of a pre-determined intensity, measuring the fluorescence emission, determining the slope of a first regression line prior to full opening of the shutter; determining the slope of a second regression line of measurements after the shutter is fully opened and determining the intersecting point between these two lines. A method of determining the corrected and normalized fluorescence emissions from a plant is provided.

33 Claims, 5 Drawing Sheets

OTHER PUBLICATIONS

An Apparatus for . . . Yields and Ouanta Abscorption Spectra . . . G. Oquist, Hallgren, Brunes—1978—21-27.

"Integrating Fluorometer for the . . . Fluorescence Induction . . . ", *Instr. Rev. Sci.*, P. Toivonen, Vivader—pp. 1687–1690, Oct. 1984, vol. 55(10).

"A New Method for the Separation . . . The Variable Fluorescence of Chlorophyll A in In Vivo", *Biomedical and Biophysical Research Comm.*, vol. 149, No. 2, Morissette and Popovic, 1987, pp. 385–390.

A Portable Microprocessor . . . Measuring Chlorophyll Fluorescence Kinetics in Stress Physiology, *Physiologia Plantarum*, vol. 73, Oquist and Wass—1988, pp. 211–217.

"Portable Solid–State Fluorometer . . . Fluorescence Induction in Plants", *Rev. Sci. Instr.*, vol. 46, No. 5, Schreiber, Groberman, Vidaver—May 1975—pp. 538–542.

"An Integrated Portable . . . Measurement of Photosynthetic . . . Light Absorption . . . Attached Leaves"—Ireland, Long, Baker, *Plant, Cell and Environment*, vol. 12, 1989, pp. 947–958.

APPARATUS AND METHOD FOR DETERMINING PLANT FLUORESCENCE

BACKGROUND OF THE INVENTION

1. Field of the Invention

The present invention relates to an apparatus and method for determining the photosynthetic activity of a plant by determining the chlorophyll fluorescence of the plant.

2. Description of the Prior Art

It is important in many areas of plant husbandry to determine the physiological condition of a plant or group of plants. For example, the forestry industry replants millions of seedlings every year. These seedlings are grown in a controlled environment and are preferably transplanted in the field during certain very specific and critical periods during seedling development. It is difficult to determine, by physical appearance alone, when a seedling has developed to a stage when transplant can occur with minimal interference with the growth cycle of the seedling. If a seedling is transplanted at the wrong time the possibility of impairing the growth of the seedling is increased. In some situations the trauma to the seedling may be such, or the development of the seedling may be at a particularly vulnerable time, that death of the seedling occurs. In addition, it is desirable in various situations to cull out plants which have been damaged by frost, high light intensity, herbicides or other inhibitors to ensure optimal plant viability and efficiency of plant husbandry operations.

In addition, it can be difficult to determine from external plant appearance whether or not the light intensity in a greenhouse or nursery setting may be optimal for plant health. Similarly a determination of plant stress, effects of fertilizer and water regimes and effects of physical damage on the plant's health is difficult if not impossible to determine based on the external appearance of the plant.

It is well known that fluorescence emission from plants and plant material is an accurate indication of the photosynthetic activity of the plant and consequently the general health and development of that plant. Devices which measure plant fluorescence in order to determine the general condition of a plant are also known. These apparatuses generally utilize an artificial light source to induce photosynthesis in the plant or portion of the plant thereby inducing fluorescence in the plant. This fluorescence can be detected by a photodetector set at the specific waveband of light corresponding to these fluorescence emissions. Alternatively, apparatuses exist wherein the light source is maintained at a level which does not induce photosynthesis and the effect of modulated high light intensity on the signal from the weak measuring light is monitored. Such a device is described in European Patent Application Number 86304543.1 published Jan. 21, 1987 under number 0209247. This device measures the $CO_2$ uptake of the plant and the light absorbed by the plant.

FIG. 1 is an example of several fluorescence emission curves from a white spruce seedling measured at various times. The $CO_2$ uptake rate taken at each sampling interval is also indicated on the graph for comparison purposes. The term APS is an abbreviation for "apparent photosynthesis rate" of the seedling. Note that the relative fluorescence emission is an indication of the "hardening off" of the seedling during the late fall or early winter season. The determination of the occurrence of "hardening off" in a seedling is important in indicating when a seedling may be safely lifted and transferred to winter storage.

If meaningful analysis and recommendations are to be provided to the greenhouse operator it is important that reproducible measurements concerning plant fluorescence be obtained and that the measurements be provided to the operator in an understandable manner. Prior art apparatuses and methods do not provide an accurate, convenient and reproducible measurement of plant fluorescence and therefore comparison between plants or between the same plant at different times does not provide the most reliable data for interpretation. Furthermore, without accurate, easily acquired, reproducible data, comparison of sample fluorescence curves with previously acquired data bank fluorescence curves obtained under established conditions, is difficult. Specifically, fluorescence curve reproduceability is affected by several factors which are not adequately monitored in prior art devices, including:

(a) differences in excitation light intensity on the plant;

(b) automatic compensation for system dark signals, that is signals caused by the detection circuitry in the absence of a fluorescence signal;

(c) automatic compensation for straylight signals caused by background light and fluorescence in the sphere when no plant is present;

(d) sufficiently reliable automatic determination of fluorescence emitted from the plant before the onset of photochemistry (the Fo level);

(e) the application of light intensity in the integrating sphere on the plant which is insufficient to induce acceptable rates of photosynthetic activity in the plant; and (f) automatic determination of net light absorbed by the sample in the sphere as a means to evaluate sample size.

There is a need for an apparatus and method for determining plant fluorescence in a reproducible manner and which can be accurately compared with fluorescence of other plants, or with the same plant over several periods of time. As well, there is a need for an apparatus and method for determining plant fluorescence which can be accurately compared with appropriate data bank fluorescence curves of a plant whose fluorescence was measured under more established conditions in order to provide accurate analysis of the health or development of the plant sample and to provide recommendations concerning the care or transplant of that plant.

SUMMARY OF THE INVENTION

The present invention provides an apparatus and method for determining plant chlorophyll fluorescence in a more accurate and reproducible manner. The apparatus includes a light intensity monitoring means which monitors the light intensity in the sphere housing the plant to ensure that the light intensity stays constant and to ensure that the light intensity is maintained above a certain minimum level near or above a point which induces net photosynthetic activity. A lamp power control, responsive to the light intensity monitoring means controls the intensity of the lamp. The control can also be adjusted by the user so that measurements of fluorescence curves at different pre-selected intensities can be obtained and compared. In addition, means are provided to adjust the fluorescence measurements to correct for the effects of system dark signals and straylight signals and to normalize the signal to eliminate Fo fluorescence from the final fluorescence value. This normalized fluorescence is used to create a fluorescence curve which may be compared with data bank curves to provide useful information about a plant or plant group.

According to the invention there is provided an apparatus for determining the photosynthetic activity of a plant, which comprises a light-impermeable chamber for housing a plant having a conduit for admitting light into the chamber, illuminating means for illuminating the plant within the chamber and controlling means for controlling the intensity of the illuminating means. The apparatus includes monitoring means, responsive the intensity of light in the chamber and communicating with the controlling means, for monitoring the intensity of light in the chamber at pre-determined time intervals and for adjusting the controlling means based on the monitored light intensity to maintain the light intensity in the chamber within a pre-determined intensity range. The apparatus also includes photosynthesis measuring means connected to the chamber for measuring the photosynthetic activity of the plant induced by said illuminating means.

The photosynthesis measuring means may be a light intensity measuring means for measuring the light intensity in the chamber corresponding to wavelengths of light which are characteristic of fluorescence emission from plants. The light intensity measuring means may include a light selecting means, which may be a light filter, which allows only light of wavelengths corresponding to the wavelengths characteristic of plant fluorescence emission to pass to the photosynthesis measuring means. The photosynthesis measuring means may be a photodiode, the illuminating means may be a D.C. powered lamp and the controlling means may be a voltage regulator.

A method of estimating the fluorescence emission from a plant in a chamber before the onset of photochemistry, the chamber having a shutter to admit light into the chamber, comprises the steps of illuminating an empty light-impermeable chamber with light of a pre-determined intensity and measuring the fluorescence emission in the chamber at pre-determined time intervals. These measurements are stored and the slope of a first regression line of measurements prior to full opening of the shutter is determined. These measurements are characterised by a rapid increase in fluorescence emission over time. The slope of a second regression line of measurements after the shutter is fully opened is then determined. These measurements are characterized by a less rapid increase in fluorescence emission over time. The fluorescence emission value which corresponds to the point of intersection between the first and second regression lines is then determined.

The method may include a determination of the slope of the first line characterized by calculating and storing the slope of a first plurality of data points on a regression line. The slope of a second plurality of data points of which a pre-determined number of data points are the same as the data points in the first plurality of data points, is then calculated and stored. The slope of the second calculation is compared to that of the first. This is repeated until the slope no longer increases and this slope value is stored as the slope of the first regression line. The method may include a determination of the slope of the second regression line characterized by determining and storing the slope of a best fit slope line fitted to the measurements taken after the shutter is fully opened.

Optionally, the intensity of the light in the chamber may be monitored and the illuminating means may be controlled so that the intensity of light in the chamber remains within a pre-determined intensity range.

A method of normalizing fluorescence emissions from a plant comprises the steps of measuring and storing the dark signal in a chamber with no outside illumination applied in the chamber and measuring and storing the straylight signal in an empty chamber with light illumination of a pre-determined intensity applied therein. A plant sample is introduced into the chamber after the application of illumination in the chamber is discontinued and the fluorescence in the chamber upon initial application of illumination in the chamber is measured at pre-determined intervals. The fluorescence of the sample in the chamber before the onset of photochemistry is estimated based on the measurement of fluorescence in the chamber on initial application of illumination. This fluorescence value is then stored. The fluorescence in the chamber is measured at pre-determined intervals over a pre-determined time period during illumination of the chamber. The measured fluorescence is corrected by eliminating the effects of dark signal and straylight signal using the formula:

$$F_{VAR}(t) = F_{meas}(t) - L_{st} - D_s$$

where:
$F_{VAR}(t)$ is the corrected fluorescence value at time t,
$F_{meas}(t)$ is the measured fluorescence at time t,
$L_{st}$ is the straylight signal, and
$D_s$ is the dark signal The corrected measurement of fluorescence over the pre-determined time period is normalized by calculation using the formula:

$$F_{VAR} = \frac{F_{VAR}(t) - F_o}{F_o}$$

where:
$F_{VAR}(t)$ is the normalized fluorescence value at time t,
$F_{VAR}$ is the normalized and corrected fluorescence value, and
$F_o$ is the initial fluorescence

DETAILED DESCRIPTION OF AN EMBODIMENT OF THE INVENTION

Figure 1:
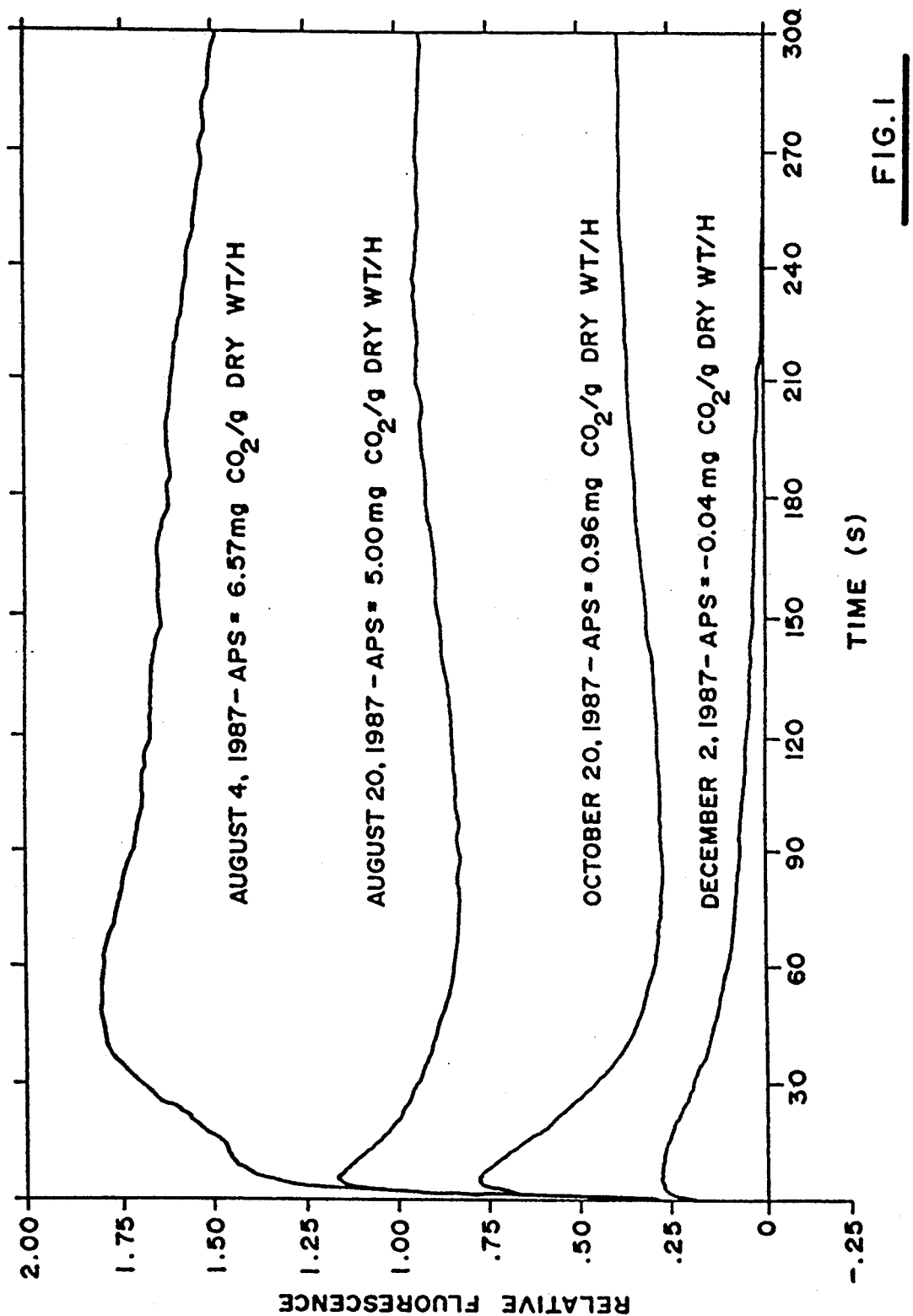
FIG. 1 is a time-base graph of the fluorescence activity of a white spruce on Aug. 4, 1987, Aug. 20, 1987, Oct. 20, 1987 and Dec. 2, 1987 to illustrate the winter "hardening-off" of the sample.
Figure 2:
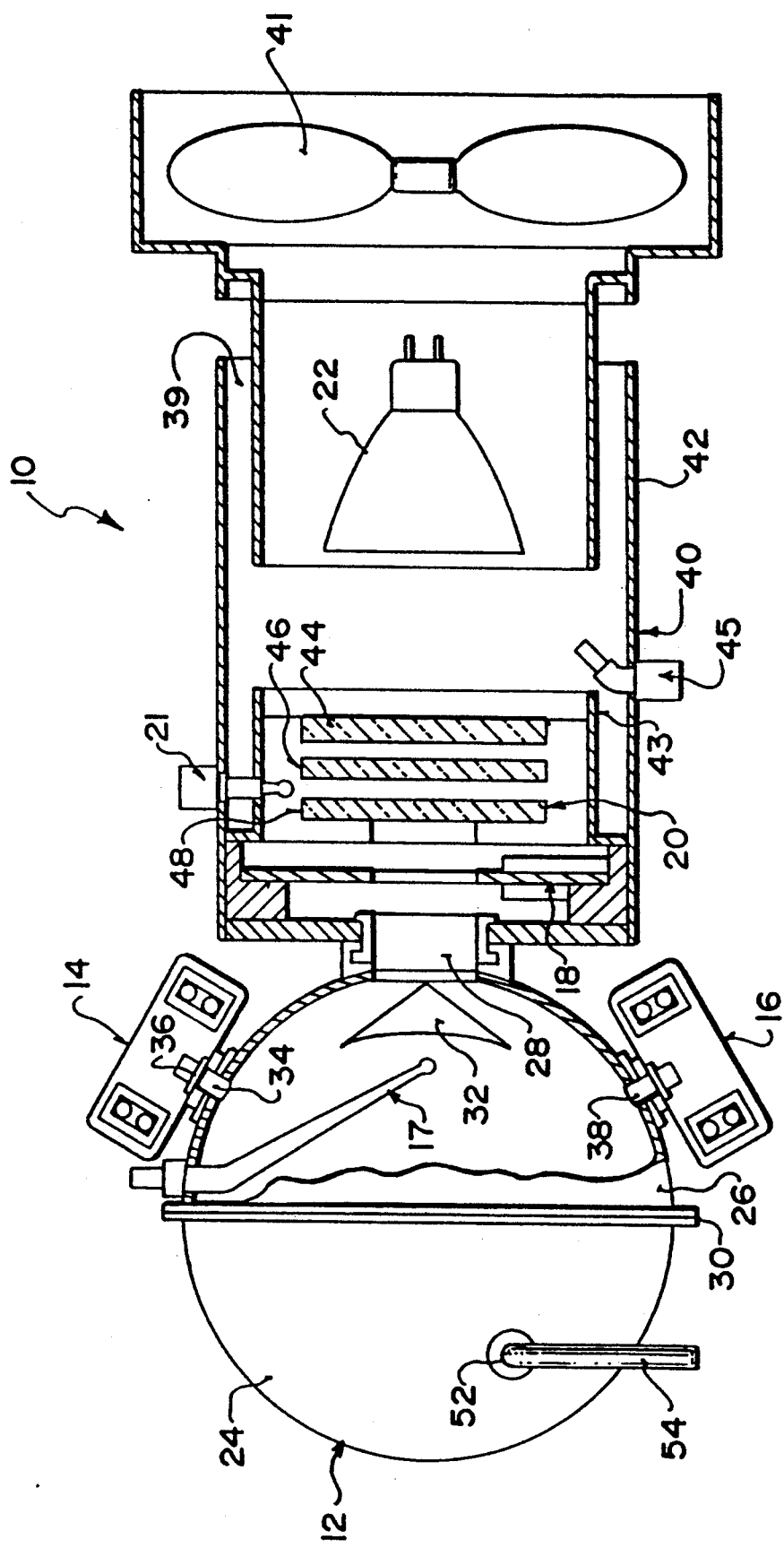
FIG. 2 is a schematic side elevation view showing the sphere probe of the apparatus for detecting plant photosynthetic fluorescence according to an embodiment of the invention.

Referring to FIG. 2 there is shown generally a sphere probe 10 having a sphere 12 for holding a plant sample, fluorescence detection unit 14, light absorption unit 16, electronic shutter 18, optical filter 20 and excitation lamp 22. It is to be understood that the words plant or plant sample used herein include all or part of a plant capable of photosynthesis.

Sphere 12 is composed of two separable hemispheres 24 and 26 coated on the inside with a highly reflective material and is generally light-impermeable. A spongy rubber gasket 30 seals the two hemispheres together to make a light and gas impermeable seal in sphere 12. Various diameter spheres may be used and the size is generally selected based on the size of the sample to be analysed.

Light port 28 extends laterally into hemisphere 26 and is used to permit introduction of excitation light from lamp 22 into the interior of sphere 12. Diffusion cone 32 is positioned within port 28 so that prefocussed light from lamp 22 will be diffused into sphere 12. Inlet 52 is attached to hemisphere 24 to permit gas from hose 54 to enter sphere 12. Outlet (not shown) is also attached to hemisphere 24 to permit an outflow of gas from sphere 12.

A fluorescence port 34 extends laterally from hemisphere 26 and is connected to fluorescence detection unit 14 to permit fluorescence within sphere 12 to be detected by unit 14. Unit 14 includes a photodetector, such as a photodiode and includes an amplifier (not shown) for amplifying the signals caused by the detection of fluorescence in sphere 12. Port 34 includes glass filters 36 such as Corning CS-7-59 and CS-2-64 filters placed in the optical path of unit 14 which cooperate to provide a band-pass filter which permits only light at wavelengths corresponding to fluorescence emission to be transmitted to unit 14. The optimum wavelength corresponding to fluorescence emission is between 460 and 625 nanometers. Sand filters permit only light of wavelengths greater than 685 nanometers to pass to unit 14. A light absorption port 38 also extends laterally from hemisphere 26 and is connected to light absorption unit 16 to permit light within sphere 12 to be detected by unit 16. Unit 16 includes a photodetector, such as a photodiode, and includes an amplifier (not shown) for amplifying the signals caused by detection of light in sphere 12. Sphere temperature probe 17 is positioned in sphere 12 to determine the temperature within sphere 12. Probe 17 is connected to an amplifier 67 (diagramatically shown in FIG. 3) and the amplified signal is transmitted to the CPU.

Figure 3:
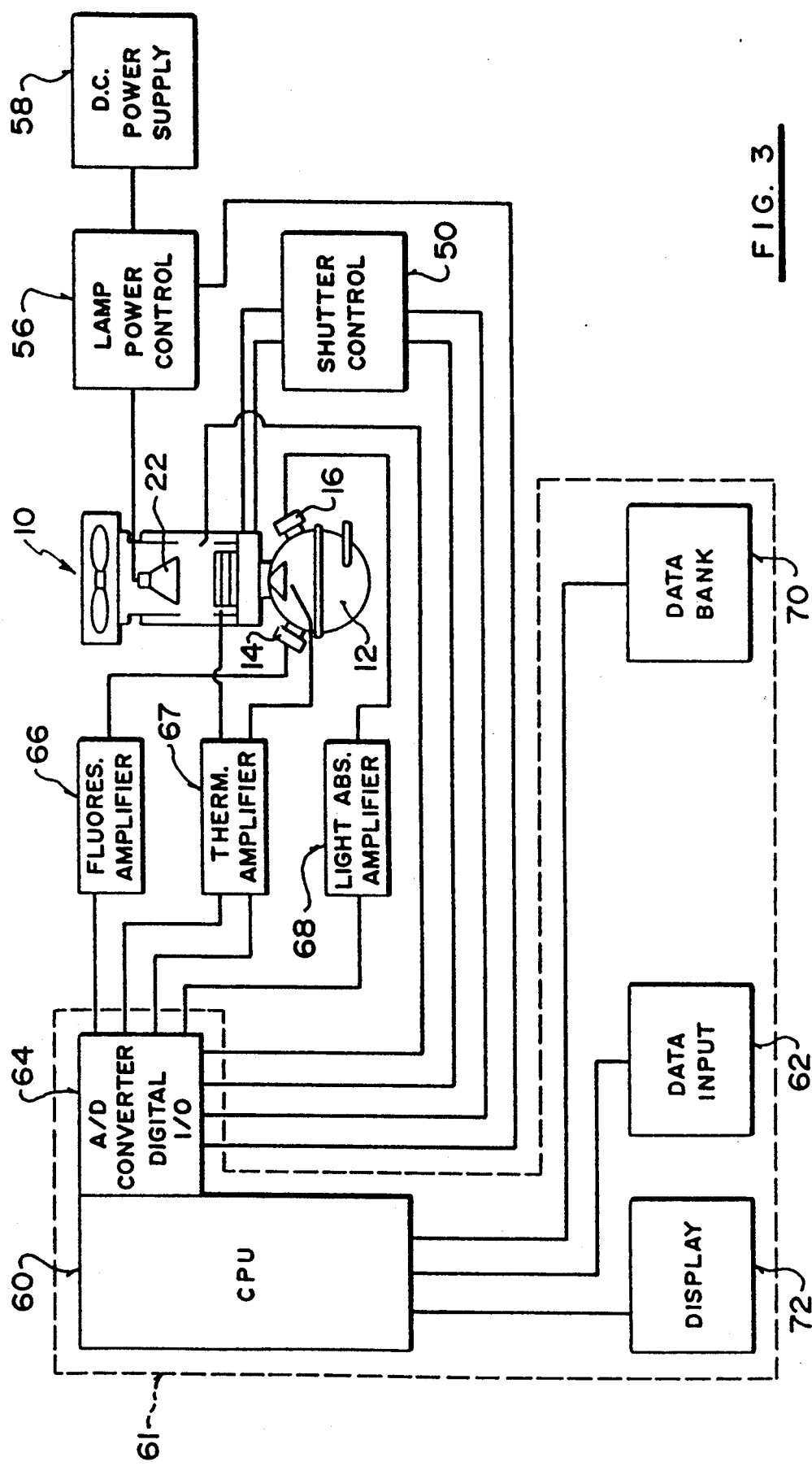
FIG. 3 is a block diagram of the apparatus according to one embodiment of the invention.

Excitation light module 40 includes housing 42 which contains filter housing 43 and lamp 22 therein Lamp 22 includes a prefocussed projector lamp (not shown) of suitable wattage powered by a battery system or a regulated DC power supply (diagramatically shown in FIG. 3 at 58). Housing 42 includes a double walled chimney 39 for minimum light leakage towards the outside of module 40. Cooling fan 41 is positioned adjacent lamp 22 to blow cooling air into housing 40. Three filters are mounted in filter housing 43 between sphere 12 and lamp 22. Filter 44 is positioned nearest to lamp 22 and filters infra-red light from the light emanating from lamp 22. Filter 44 may be water cooled. Corning C5-3-71 filter 46 is positioned in the light path adjacent filter 44. Corning CS-4-96 filter 48 is positioned adjacent filter 46 between filter 46 and shutter 18. These filters isolate the excitation waveband and permit only this waveband to transmit through the filters to shutter 18. Shutter 18 is positioned in the light path between filter 48 and port 28 and is controlled by a shutter control 50 (shown diagramatically in FIG. 3). Filter temperature probe 19 is located within filter housing 43 to detect and determine the temperature within filter housing 43. A signal from probe 19 is amplified by amplifier 67 (diagramatically shown in FIG. 3) and the amplified signal is transmitted to the CPU 60. Probe 19 is used to detect excess heat conditions on filters 44 and 46 as these filters are very sensitive to excess heat conditions. Light sensor 45 is positioned within housing 42 to monitor the light intensity generated by lamp 22. The user may then adjust the light levels of lamp 22 by monitoring sensor 45 with lamp 22 on. The signal from sensor 45 is directed to CPU 60 for processing by computer 61.

Referring to FIG. 3, the apparatus is controlled by Computer 61 such as a personal computer The personal computer includes a central processing unit (CPU) 60 which runs a software program for controlling the apparatus. The personal computer also includes a memory storage device 70 such as a floppy disc or other non-volatile media. The contents of the memory are used in the analysis of samples in sphere 12 or to compare and process sample data in computer 61. The computer also includes a display device 72 which in this example is a video display monitor. The monitor displays output data and system information such as self-test status, operating functions, raw and processed data, program menus for data acquisition, program menus for processing, and program menus for analysis and interpretation. A printer or plotter may also be connected with computer 61 to provide hard copies of system functions such as fluorescence plots.

The computer is controlled by a data input device such as a standard personal computer keyboard. The keyboard is used to allow the operator to enter data and commands to control the operation of the program and hence the operation of the apparatus.

The computer is connected to an input/output device 64 which includes an analog to digital converter and digital input/output (I/O functions). The analog to digital converter is addressed by the CPU 60 to configure the analog to digital converter to receive signals from either the fluorescence amplifier 66 or the light absorption amplifier 68. The CPU can therefore read data from the analog to digital converter corresponding to the light detected at units 14 and 16 respectively.

The digital I/O functions of input/output device 64 are connected to the shutter control 50 and to a lamp power control 56. The program can control the shutter 18 by directing the CPU 60 to issue signals to the digital I/O functions of the input/output device to send further signals to the shutter control 50. The shutter control 50 provides the operating voltage to open and close shutter 18 thereby controlling whether or not light from lamp 22 enters the inside of sphere 12. Shutter control 50 also issues a trigger signal back to the digital I/O function and hence back to the CPU 60 and program to initiate fluorescence measurement.

The program can also control the light intensity of the lamp 22 by directing the CPU 60 to issue signals to the digital I/O functions of the input/output device 64 which in turn issues signals to the lamp power control 56. The lamp power control varies the light intensity by controlling the power from a DC power supply 58. The power to the lamp is varied by the lamp power control 56 to effect changes in light intensity from the lamp. Control of the light intensity emanating may be performed manually by an operator through keyboard commands or may be done automatically under program control.

The program monitors light levels of the lamp when the shutter is closed and issues signals to the digital I/O functions of the input/output device 64 which in turn issues signals to the lamp power control 56.

The program monitors temperature levels in the sphere probe and issues signals to the operator to indicate if levels are outside the physiological range for adequate interpretation of the fluorescence results. Fluorescence signals are then tagged with the temperature data for further analysis.

The software program monitors temperature in the filter cooling system to indicate to the user if the temperature is above a critical level. Since those filters are fairly sensitive to heat this warns the operator if the cooling system is operating outside of optimal temperature conditions

OPERATION

The operation of the embodiment described above will now be described with reference to FIG. 2, 3, 4 and 5.

An important step in ensuring that the data obtained from the apparatus is reproducible and that meaningful information can be derived from the fluorescence measurements is to maintain the light intensity in sphere 12 at a constant level during the operating of the apparatus. This is done by turning lamp 22 on and opening shutter 18 to introduce light into the sphere and measuring the intensity using light absorption unit 16. Intensity of lamp 22 is adjusted by varying the voltage to the lamp using lamp power control 56. Control 56 is controlled by computer 61 either automatically pursuant to a preselected intensity value or by the operator entering an appropriate intensity level on keyboard 62 of computer 61. Measurement of light intensity can be made from time to time either automatically or by the operator controlling computer 61 to ensure constant intensity during the operation of the apparatus.

In most cases, it is preferable to maintain light intensity in the sphere above or at least near the "light compensation point" of the sample being tested. The "light compensation point" is the minimum intensity of light which will induce net photosynthetic activity. Once the light intensity (Io) in the sphere has been appropriately set, the program directs the CPU 60 to issue a signal to the shutter control 50, shutter 18 is closed and the amplitude of the signal from the light sensor 45 is determined and stored for later comparisons. The amplitude of a Dark Signal (Ds) from detector 14 and 16 are measured.

Once the light intensity in the sphere has been appropriately set, the program directs the CPU 60 to issue signals to the shutter control 50, shutter 18 is closed and the amplitude of a Dark Signal (Ds) is measured. The Dark signal is the background signal caused by the electronic components in the apparatus, including the electronic noise of the system. The Dark Signal is measured with no light entering sphere 12 and no sample in the sphere. With the apparatus in this dark condition, CPU 60 reads the signals from units 14 and 16 processed by the A/D converter in input/output device 64. A plurality of readings may be taken from each of units 14 and 16, the readings being averaged by the program to provide the Dark Signal value. A determination of Dark Signal value can also be made by averaging the first data points obtained upon commencement of a sample run as it takes about 1 millisecond for shutter 18 to be energized, during which time shutter 18 remains closed. The Dark Signal value is stored by computer 61 in memory device 70 for future use.

Straylight Signal ($L_{sl}$), the background fluorescence in the sphere, is then determined. The program directs the CPU 60 to read the signal from unit 14 processed by the A/D converter, when the shutter is open to admit light in the empty sphere. Again, several data points may be obtained with the results averaged to improve reliability of the Straylight Signal. The Straylight Signal value is a function of light intensity and if light intensity is changed this value must be redetermined. This is one reason why it is important to maintain a constant light intensity in the sphere in order to permit accurate comparison of test results. The Straylight Signal ($L_{sl}$) is also stored by computer 61 in memory device 70 for use in subsequent calculations. The program deducts the Dark Signal and Straylight Signal values from the test fluorescence data to eliminate the contribution of each from the data collected. The program directs the CPU 60 to read the signal from unit 17 processed by the A/D converter to determine temperature levels in the sphere and to test if the value is within an accepted pre-determined physiological range. The program directs the CPU 60 to read the signal from unit 21 processed by the A/D converter to determine temperature levels in the filter housing 43 and test if the value is within an accepted pre-determined range for satisfactory protection of the filters. The program will direct the CPU 60 to issue a signal to the operator to indicate a fault in the cooling unit of filter housing 43.

The program then directs shutter control 50 to close shutter 18, and the program enters a waiting routine to enable the operator to place a plant sample between hemispheres 24 and 26. The sphere is closed around the sample and data may be taken. Hemispheres 24 and 26 are then sealed in a manner which prevents light from entering the sphere from outside apparatus 10. The program directs the CPU 60 to routinely and sequentially read units 17, 21, and 45 to ensure the temperature in the sphere and temperature in the cooling system are adequate and to control light levels in the light module until the shutter is opened for fluorescence measurement. The program directs the CPU 60 to issue a signal to activate shutter control 50 which opens shutter 18. Shutter control 50 simultaneously sends a signal back to the CPU 60 and hence the program to initiate the data collection process for that sample. The data collection process occurs under program control and involves reading signals from unit 14 processed by the A/D converter. Readings are taken at a high frequency initially (ie $10^4$/secs.) and at a lower frequency thereafter.

Initial data is used to estimate the fluorescence emitted by the illuminated sample before the onset of photochemistry in the sample, called the Fo emission level. Fo emission must also be deducted from each fluorescence reading to obtain readings corresponding only to fluorescence due to photosynthesis. This permits accurate reproducibility and comparability of the results of different samples. During the first ten milliseconds, readings are taken at a high frequency, preferably above 10,000 per second, to provide a more accurate estimate of Fo as described more fully below.

Figure 4:
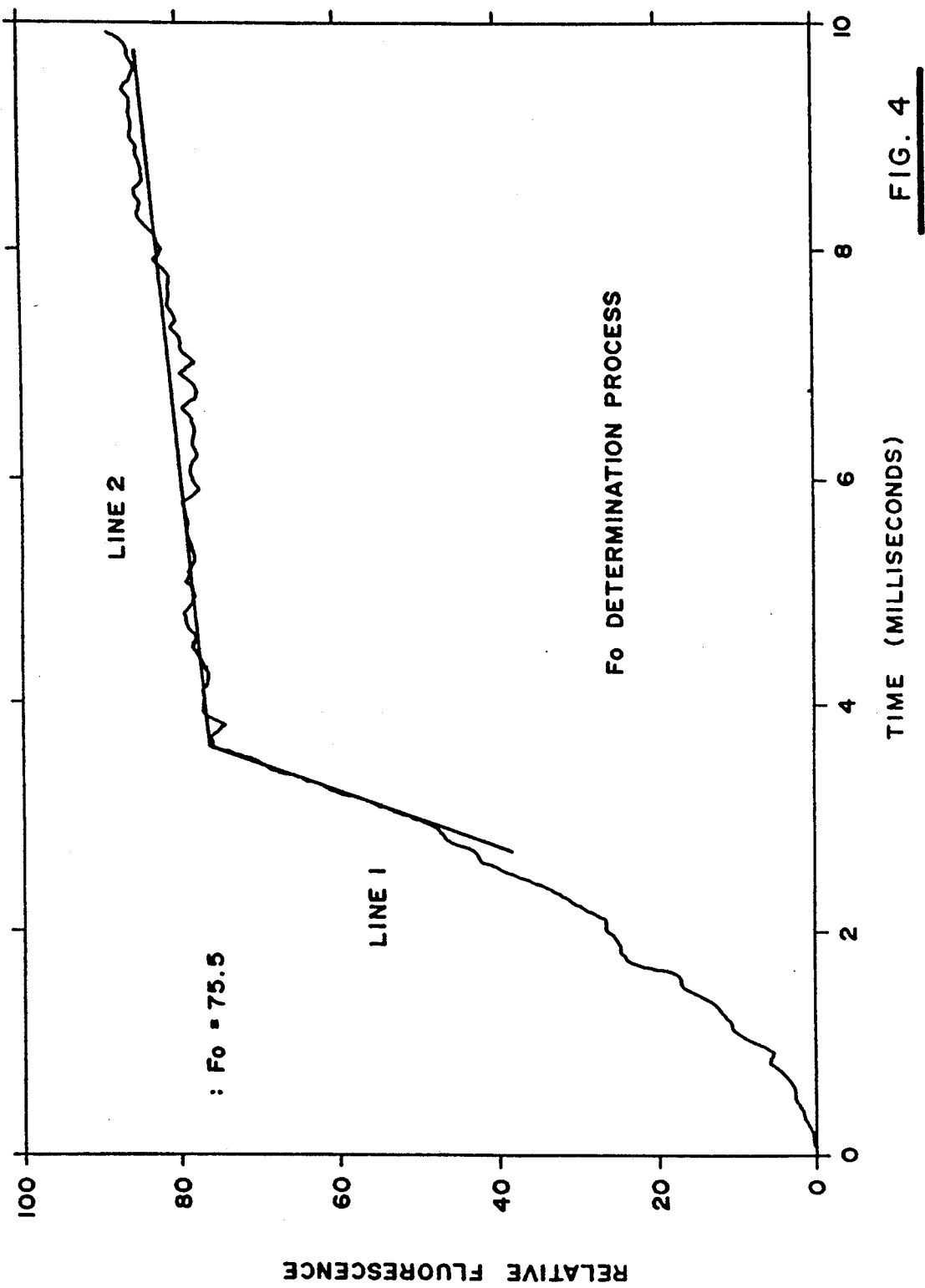
FIG. 4 is a time-base graph illustrating the fluorescence curve in the first 10 milliseconds of illumination with slope lines superimposed thereon illustrating the calculation of Fo.
Figure 5:
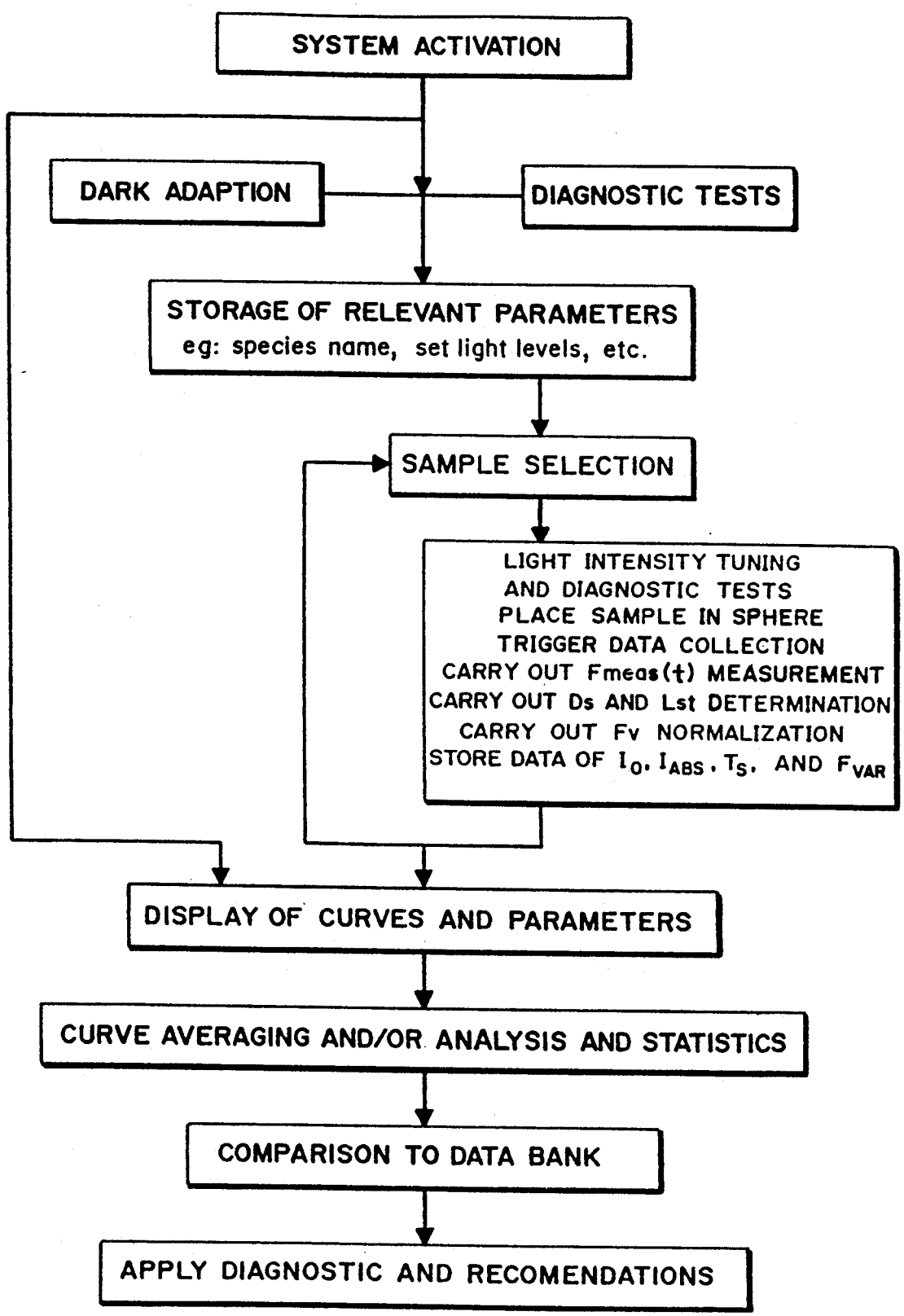
FIG. 5 is a flow-chart illustrating the general method of the invention

FIG. 4 is a plot of relative fluorescence versus time of initial fluorescence readings from unit 14. The response time of fluorescence from the plant due to illumination is $10^{-9}$ seconds Therefore, any changes in illumination intensity at the plant will be seen almost instantaneously as changes in fluorescence from the plant. The shutter takes in the order of $3 \times 10^{-3}$ seconds to open fully and therefore the light intensity in the sphere varies from zero to full illumination over a period on the order of $10^{-3}$ seconds. The fluorescence from the plant follows the illumination and therefore varies from zero to a first breakpoint value during the time the shutter is opening. The initial steep slope in the graph up until the first breakpoint is due to the time it takes for shutter 18 to open fully. The gradual slope after the first breakpoint is mainly due to fluorescence of the plant caused by photosynthesis. The breakpoint of the curve corresponds to the Fo value. The breakpoint is estimated by the program by calculating the intersection point of a first approximation slope line (first regression line) for the steep region (line 1) with a first approximation slope line for the gradual slope region (second regression line) (line 2).

Line 1 is determined by the program by estimating the slope of the line passing through the first fifteen data points. Then the slope of a second line passing through the last ten of these fifteen data points and five next adjacent data points is determined and compared to the previously calculated slope value. This process is repeated until the slope values no longer increase. This constant slope value is the slope of line 1 of FIG. 4.

Line 2 is calculated by the program by using data points in the gradual slope region only (that is, data points taken from the time the shutter is fully open to the 10 millisecond point). A best fit slope line is fitted to these data points in a manner which is commonly known.

The intersection point of line 1 with line 2 corresponds to the estimate of the first breakpoint and the Fo value. In FIG. 4, the estimated Fo value has been determined to be 75.5 relative fluorescence. The Fo value is stored by the computer in memory device 70 for later use by the program in calculating a normalized fluorescence value. It must be understood that Fo will vary depending on the sample and that FIG. 4 is only one example of a calculation of Fo in a particular instance.

After the initial ten millisecond period the program reduces the frequency of data collection to between 1 to 100 data points per second for the balance of the data collection period. The length of any particular data collection period can be determined by the operator and is usually based on the nature of the information desired. This data is also stored by the computer in memory device 70 and is used by the program to construct a fluorescence versus time graph for comparison with other such graphs. Once sufficient data is collected, the program directs the CPU to issue signals to the shutter control 50 which closes shutter 18. The plant may then be removed from sphere 12.

The data obtained (F meas) is then corrected by the program to eliminate the effects of Dark Signal and Straylight Signal and then normalized to eliminate the effect of Fo on the fluorescence reading. The computer program calculates this using the following formulas based on the data obtained and stored as described above:

$$F_{VAR}(t) = F_{meas}(t) - L_{st} - Ds \quad (1)$$

where
$F_{VAR}(t)$ is the corrected fluorescence value at time t,
$F_{meas}(t)$ is the measured fluorescence value at time t,
$L_{st}$ is the straylight signal, and
$Ds$ is the dark signal $$F_{VAR} = \frac{F_{VAR}(t) - Fo}{Fo} \quad (2)$$

where
$F_{VAR}(t)$ is the corrected fluorescence value at time t,
$F_{VAR}$ is the normalized fluorescence value, and
Fo is the estimated Fo value The $F_{VAR}$ values and a fluorescence versus time graph of these values as an $F_{VAR}$ curve is stored by the computer in memory device 70 for further analysis. For every $F_{VAR}$ curve parameters such as the following may be determined: Initial light intensity (Io), light absorbed ($I_{ABS}$) temperature in the sphere during $F_{VAR}$ determination ($T_{FV}$), the Fo value of the sample, time of the day and date of the measurement.

In order to assess a group of plants the process of determining the $F_{VAR}$ curve is repeated for several samples. The program averages each $F_{VAR}$ curve at each sampling point with previously collected curves from that group to obtain a more representative $F_{VAR}$ curve for the group. Any number of $F_{VAR}$ curves may be obtained and, in practice, new sample curves are added until no appreciable change in the curve is observed. Data obtained in this way can usually be considered representative of a large population of plants.

Memory device 70 contains a library of $F_{VAR}$ curves which can be selected by the operator or the computer to be used to analyse and compare the sample $F_{VAR}$ curves in order to provide information about the sample and to provide recommendations to the operator. The library $F_{VAR}$ curves are obtained by conducting sample runs under established conditions and having the program calculate $F_{VAR}$ curves for these samples. A library of $F_{VAR}$ curves of such samples under various known conditions is input and stored in the memory device 70. This permits comparison of a particular test sample $F_{VAR}$ curve (or an average $F_{VAR}$ curve representative of a group of test samples) with a data bank $F_{VAR}$ curve or series of curves of a control sample or samples taken under the same or similar conditions as the sample or sample group.

The operator can then compare this data and make appropriate adjustments in the plant environment, for example, or determine whether plants can be transplanted to a forest or even determine the general health or viability of a sample or a group of samples at periodic intervals, say weekly or monthly. The computer software program is also designed to compare these curves and provide this information to the user with recommendations to the user. For example, the development stage of the plant or group, stress levels, viability, physiological shut-down ("hardening-off") can all be determined, depending on the purpose of the analysis. This can be done either directly by a knowledgeable operator or by the computer software which can automatically conduct the analysis and provide this information to the user.

The purpose of the computer software program is to collect fluorescence and light quanta parameters respectively emitted and absorbed by plants of which chlorophyllous pigments have been induced to photosynthesis. The apparatus controlled by this software is called the SFU INTEGRATING FLUOROMETER and takes advantage of the I/O functions provided by an A/D converter card used to interface the software with the latter. The source code was originally developed using the Microsoft QUICK BASIC language and integrates call subroutines necessary to the functioning of the A/D converter as previously described.

I The data acquisition software was developed to provide the following functions:

(a) By using the signal from the sphere light level photodetector, to measure and adjust excitation light intensity Io and to ensure that it is at a constant and sufficient level to stimulate usable fluorescence emission from the sample. Measurement of the light levels, precalibrated with the LICOR LI-185A (LICOR model LI-185A light meter fitted with a quantum flux detector head; Licor Inc., Lincoln, Nebr.), provides an accurate estimate of incident light intensity Io (without the sample) and an estimate of sample light absorption $I_{ABR}$ (with the sample in the sphere). Determination of $I_{ABR}$ is accomplished by the following calculation:

$$I_{ABR} = Io - Is$$

Is is the light level in the sphere when the plant sample is present.

(b) Correcting for dark signal (Ds) and straylight signal (Lst) from the fluorescence photodetector circuit:

(i) Determination of system dark signal (Ds) Data collection is set to start as the shutter is triggered to open. The electrical energization of the shutter coils takes about 1 ms. This allows time to collect enough data points to determine Ds which is the contribution of the detection circuits in the absence of fluorescence signal. An average of the first 15 data points is used to estimate the height above the abcissa. This value establishes Ds (FIG. 4).

(ii) Determination of straylight signal ($L_{ST}$). $L_{ST}$ is determined using the same mathematical method as for the determination of Ds when the plant is absent from the sphere. $L_{ST}$ also corrects for unwanted background fluorescence. $L_{ST}$ is directly proportional to Io, $L_{ST} = K_{ST} \times Io$. Therefore $L_{ST} = K_{ST}(Io - I_{ABR})$ in the presence of a sample. The determination of $K_{ST}$ may be done prior to a session. Net fluorescence can thus be expressed as the following:

$$F(t) = F_{meas}(t) - L_{ST} - Ds$$

where F(t) is any measured fluorescence value after the shutter is completely open. $F_{meas}(t)$ is the uncorrected signal at time t.

(c) Determination of Fo

Fo is the fluorescence emitted by the sample chlorophylls (minus reabsorption) before the onset of photochemistry and is a measure of the total number of excited chlorophyll molecules. The kinetics of the increase in light intensity within the sphere during shutter opening and the light intensity dependent rise in $F_{VAR}$ are nearly similar and do not influence the calculation of Fo appreciably. The Fo rise-time is about $10^{-3}$s. Since the shutter opening time is on the order of $10^{-3}$s the value of Fo must be corrected for the shutter opening time using a double regression algorithm applied to the initial fluorescence signal rise. This is achieved by determining two regression line equations and estimating the value of the point where they meet. The slope value of line 1 (FIG. 4) is found by taking 15 data points along the function and determining the slope of the straight line passing through them; the process is repeated by shifting these 15 data points by 5 other data points (in other words they overlap by 10 data points) until the slope ceases to increase. When the maximum slope is determined the values are kept to draw a final regression line. A second regression line (line 2) is determined with the remaining data points of the initial 10 ms portion of the entire signal. The point where these two regression lines meet is called Fo. Once Fo is obtained its value is stored for subsequent data processing. The slope of the second regression line is stored for further analysis since it refers to the rate of reduction of the $Q_A$ pools. Measurement units of Fo are in mV;

(d) To acquire and store the time course fluorescence emission data ($F_{VAR}$) This requires two different sampling rates for each sample; one during the initial phase of emission to obtain a Fo value at $>10^4$ points $s^{-1}$ and another much slower rate (1 to $10^2$ points $s^{-1}$) selected by the user and determined by the nature of the information desired;

(e) To normalize the data of the completed fluorescence time courses. The purpose is to remove the contributions of Ds and $L_{ST}$ (described above) and initial (fluorescence emission amplitude) when comparing data from different samples or when averaging the responses of several samples. This is accomplished by subtracting the Fo value from each data point of the emission time course using the relationship, $$F_{VAR} = \frac{F_{VAR}(t) - Fo}{Fo}$$

where Fo is the total fluorescence emission signal at time t. Fo is the stored value of the initial emission in mV as calculated in (c) and $F_{VAR}$ is the relative variable fluorescence emission;

(f) To average time courses of normalized fluorescence emission. This is accomplished by adding the corrected values $F_{VAR}$ at each corresponding sampling point on the fluorescence emission time course, excluding the segment used to determine the Fo, and dividing by the number of samples. Any number of samples can be averaged and in practice, new samples can be added until no appreciable change in the time course is observed Data obtained in this way can be considered to be representative of a large population of plants;

(g) To support a baseline data bank which is used to evaluate and interpret $F_{VAR}$ in relation to the performance of similar samples previously assessed under the same physical conditions as the current test samples. This permits comparison of current samples with previously selected samples of known performance;

(h) To provide user instructions for each data acquisition, processing, and analysis step and tutorials for overall operation of the system;

(i) To provide menu-driven access to the baseline data bank which permits user to input information regarding current sample material in order to ensure that input data is matched by appropriate stored data;

(j) To compare newly acquired data with stored data and evaluate it in relation to established responses of particular species or varieties under conditions similar to the test conditions of the sample plant, for example: development stage, stress levels, viability, photoinhibition and physiological shutdown. This is done either visually or with a software program which compares new data with data stored in a library-file containing $F_{VAR}$ curves previously interpreted and relevant to the test;

(k) To display any previously collected data to screen monitor and/or either produce a hard copy on a pen plotter or printer; and (l) To carry out all the operations listed in (a–j) above with a minimum of user intervention.

Outline of processes

1. Introductory blocks:
(a) find the number of bytes of memory available for installation of the software and its use in the computer; if memory is insufficient then warns the operator;
(b) defines variables and types of variables;
(c) declares shared variables for all modules of the program; and
(d) defines various data arrays.

2. Assessment of various machine I/O ports for optimal functioning
(a) DOS version;
(b) Time and Date;
(c) Type of video adapter installed;
(d) Is the A/D converter installed?
(e) Is the input device "mouse" installed?

3. Install software interfaces with the various output devices by uploading a previously saved customized configuration; if it does not exist, the operator is prompted to enter the name of the various components of the interfacing computer system.

4. Main menu
(a) the operator is offered three choices;
  1. Collect new fluorescence data;
  2. Display and analyze previously saved data; and
  3. Change configuration.

4.1 Collect new fluorescence data
(a) Diagnostic tests
  Test if the fluorometer instrument is responding by issuing signal to the shutter control device to open the shutter and verify if all digital outputs are in the range of values expected. If devices are not responding and/or adjusting adequately the program will issue signals to the operator. Close shutter;
  Turn on lamp (if not already on) to present voltage;
  read signals from the excitation light module photodetector; if level too high or too low then the program issues signal to the lamp voltage control device to vary the voltage of the lamp circuit and adjust light levels to preset level;
  read signal of temperature probe from filter cooling system. If temperature is exceeding a preset level then the program issues signal to the operator to remedy;
  read signal from sphere light photodetector. If level, when shutter is closed, exceeds a minimum preset value then the program issues a signal to the operator to close the sphere if opened.

(b) Straylight in the fluorescence region ($L_{ST}$) and light level determination (Io)
  read fluorescence photodetector signal, determined value of the fluorescence dark signal (Dsf);
  read sphere light photodetector signal, determined value is the light dark signal (Dsl);
  the program issues signals to shutter control device to open shutter;
  read fluorescence photodetector signal, determined value minus Dsf is the $L_{ST}$;
  read the sphere light photodetector signal, determined value minus Dsl is the Io;
  light to straylight coefficient is calculated from:

$$K_{ST} = L_{ST}/I_o;$$

issue signal to close the shutter;
  read light module photodetector to establish reference with light levels in the sphere. Until fluorescence determination of the sample is initiated, the program will maintain light levels by periodically reading the light module photodetector signal and correcting light levels by controlling the light power supply accordingly.

(c) Keyboard entry of classification parameters relevant to the plant material being tested
  sample name;
  species name;
  seedlot reference number;
  keywords relevant to the classification scheme of the sample(s) being tested (d) Revise or change if necessary the configuration of data collection parameters (defaults set in paragraph 3 above) such as rate of sampling and duration of the sampling (from seconds to minutes)

(e) Place sample in the sphere and initiate data collection
  issue signal to open shutter;
  issue signal to CPU to establish a D.M.A. operation (a D.M.A. or Direct Memory Access operation allows maximum rates of data transfer to memory for further access);
  before shutter electrically activates or during first millisecond of data collection read fluorescence signal to determine Dsf, read sphere light photodetector to determine Dse;
  once a preset number of data points are collected at 25 KHz sampling rate, change sampling rate to 50 Hz for data collection of the remaining portions of the fluorescence signal;
  read signal from temperature probe in the sphere at the plant level and determine Ts;
  close shutter.

(f) Fluorescence data correction for straylight ($L_{ST}$) and dark signal (Ds) contributions:
  for every data points of the sphere light level data array, $$Is = I_{meas}(t) - Dsl$$

$$I_{ABS} = Io - Is$$

maximum value of $I_{ABS}$ is determined and $L_{ST}$ is calculated from:

$$L_{st} = K_{ST} \times I_s$$

for every data points of the fluorescence data array, $$F_{VAR}(t) = F_{meas}(t) - L_{ST} - D_{sf}$$

(g) Estimation of Fo is accomplished by applying the double regression algorithm to the fluorescence signal data points collected at 25 KHz for 10 milliseconds. Fo is then determined as described above under paragraph I(c)

(h) Normalization refer to paragraph I(e)

(i) Display normalized fluorescence signal to the screen monitor device of the computer. The operator is given the choice of either saving the information on a storage media such as computer disk or deleting the displayed data curve For every sampling, the fluorescence data curves are tagged with the following information:
1. Date and time of data collection;
2. Name of the sample and species name;
3. Seedlot or reference number;
4. Keywords relevant to the classification scheme of the sample(s) being tested;
5. Frequency and duration of the data collection;
6. The excitation light levels Io and light absorbed $I_{ABS}$;
7. Change in light intensity during the data collection by determining the difference in the light module light levels before minutes after data collection. All data files are saved in ASCII codes to permit easy access and retrieval by other software packages such as Database spreadsheet programs;

(j) At this stage of the operations, the operator is offered the choice to either exit the data collection subroutine or carry on to the next sampling of fluorescence. In the latter case, the program will loop back to 4.1(a) above and repeat the process with subsequent sampling;

(k) before exiting the data collection subroutine the program will issue signals to deactivate the lamp power supply.

4.2 Display and analysis of previously saved data curves
(a) Display single data curves with accompanying parameters;
(b) Averaging several data curves with statistical analysis of accompanying parameters;
(c) Plotting of graphs of either single or composite data curves on a hardcopying device such as printer or pen plotter 4.3 Change configuration of the computer system As an optional added element the apparatus can be used to estimate the weight of a plant which is another indication of plant development and viability. This can be used to assist the user in the proper care or transplanting of a plant. The amount of light absorbed by a plant is an excellent indicator of plant size and correlates with a high degree of confidence with the plant's dry weight. Since sphere 12 is coated with a highly reflective coating the only dissipation of light should be by absorption by the plant. Therefore, the amount of light absorbed by the plant is equal to the difference of light intensity in the sphere in the absence of the plant and the light intensity when the plant is present. It is important to measure light absorption with the plant in the sphere at the onset of light induction as light induction will alter the photochemical reaction of the plant leading to a change in absorption of light. The light intensity in the sphere in the absence of the plant can be measured using unit 16 while $L_{st}$ is being determined by unit 14. The light intensity in sphere 12 containing a plant sample is determined from the data points collected at the onset of full opening of shutter 18, that is within the first three milliseconds of light entry in the sphere. A regression analysis is used on these datapoints to determine light absorption at the onset of shutter full opening.

As a further option these initial data points may be used to determine the status of shutter 18 and the opening speed thereof. The computer can automatically check these parameters and signal the operator if there is a problem with shutter 18.

Various changes and modifications in the apparatus and method as herein described may occur to those skilled in the art, and to the extent that such changes or modifications are embraced by the appended claims, it is to be understood that they constitute a part of the present invention.

We claim:

1. An apparatus for determining the photosynthetic activity of a plant, comprising:
   (a) a chamber having light impermeable walls for housing a plant, said chamber having a conduit for admitting light into the chamber;
   (b) illuminating means for illuminating the plant through the conduit;
   (c) controlling means for controlling the intensity of the illuminating means;
   (d) monitoring means, responsive to the intensity of light in the chamber and communicating with the controlling means, for monitoring the intensity of light in the chamber at pre-determined time intervals and for adjusting the controlling means based on the monitored light intensity to maintain the light intensity in the chamber within a pre-determined intensity range; and
   (e) photosynthesis measuring means connected to the chamber for measuring the photosynthetic activity of the plant induced by light from said eliminating means.

2. An apparatus as described in claim 1 wherein the intensity range is between 0 and 700 micro moles of photons per square meter per second.

3. An apparatus as described in claim 1 wherein said photosynthesis measuring means is a light intensity measuring means for measuring the light intensity in the chamber corresponding to the wavelengths of light which are characteristic of fluorescence emission from a plant.

4. An apparatus as described in claim 3 wherein said wavelength is between 460 and 625 nanometers.

5. An apparatus as described in claim 3 wherein said light intensity measuring means further comprises a light selecting means for allowing only light of wavelengths corresponding to the wavelengths characteristic of plant fluorescence emission to pass to said light intensity measuring means.

6. An apparatus as described in claim 5 wherein said light selecting means is a light filter which permits only light of wavelength greater than 685 nanometers to pass to said light intensity measuring means.

7. An apparatus as described in claim 3 wherein the light intensity measuring means is a photodiode.

8. An apparatus as described in claim 1 wherein the illuminating means is a D.C. powered lamp and the controlling means is a voltage regulator.

9. An apparatus as described in claim 1, further comprising:
(a) light introduction means for introducing light from the illuminating means into the chamber in a virtually instantaneous manner.

10. An apparatus as described in claim 9 wherein the light introduction means is a shutter.

11. An apparatus as defined in claim 1 further comprising analysing means for recording and analysing signals from the photosynthesis measuring means.

12. An apparatus as defined in claim 11 wherein said analysing means further comprises converting means for converting analog signals from the photosynthesis measuring means into digital signals for the analysing means.

13. A method of estimating the fluorescence emission from a plant in chamber before the onset of photochemistry, the chamber having a shutter to admit light into the chamber, comprising the steps of:
(a) illuminating a chamber having walls impermeable to light and a conduit for admitting light into the chamber, with light of a pre-determined intensity, said chamber containing a plant;
(b) measuring the fluorescence emission in the chamber at pre-determined time intervals and storing the measurements, said measurements forming a graph line of measurements over time having an initial relatively rapid increase in fluorescence emission over time and having a subsequent less rapid increase in fluorescence emission over time;
(c) determining the slope of a first regression line of measurements prior to the full opening of the shutter, being characterized by said relatively rapid increase in fluorescence emission over time;
(d) determining the slope of a second regression line of measurements after the shutter is fully open, being characterized by said less rapid increase in fluorescence emission over time; and
(e) determining the fluorescence emission value corresponding to the point of intersection between the first and second regression lines.

14. A method as described in claim 13 wherein the determination of the slope of the first regression line comprises:
(a) calculating and storing the slope of a first plurality of data points on a regression line;
(b) calculating and storing the slope of a second plurality of data points of which a pre-determined number of data points are the same as the data points in the first plurality of data points;
(c) comparing the slope of the second calculation to that of the first; and
(d) repeating steps (b) and (c) until the slope no longer increases and storing the constant slope value as the slope of the first regression line.

15. A method as described in claim 14 wherein the determination of the slope of the second regression line comprises:
(a) determining and storing the slope of a best fit slope line fitted to the measurements taken after the shutter is fully opened.

16. A method as described in claim 13 wherein the pre-determined time interval is at least 10,000 measurements per second.

17. A method as described in claim 13, further comprising:
(a) monitoring the intensity of the light in the chamber; and
(b) controlling the intensity of light in the chamber so that the intensity remains within a pre-determined intensity range.

18. A method as described in claim 13, further comprising:
(a) monitoring the intensity of the light source; and
(b) controlling the intensity of light from the light source so that the intensity of light in the chamber remains within a pre-determined intensity range.

19. A method of determining the corrected and normalized fluorescence emission from a plant, comprising the steps of:
(a) measuring and storing a dark signal in a chamber with no outside illumination applied in the chamber;
(b) measuring and storing the straylight signal in an empty chamber with light illumination of a pre-determined intensity applied therein;
(c) introducing a plant sample into the chamber after the application of illumination in the chamber is discontinued;
(d) measuring and storing the fluorescence in the chamber at pre-determined intervals upon initial application of illumination in the chamber;
(e) estimating and storing the fluorescence of the sample in the chamber before the onset of photochemistry based on the measurement of fluorescence in the chamber on initial application of illumination;
(f) measuring and storing the fluorescence in the chamber over a pre-determined time period at pre-determined intervals during illumination of the chamber;
(g) correcting the measured fluorescence by eliminating the effects of dark signal and straylight signal using the formula:

$$F_{VAR}(t) = F_{meas}(t) - L_{st} - D_s$$

where:
$F_{VAR}(t)$ is the corrected fluorescence value at time t
$L_{st}$ is the straylight signal, and
$D_s$ is the dark signal;
(h) normalizing the measurement of fluorescence by using the formula:

$$F_{VAR} = \frac{F_{VAR}(t) - F_o}{F_o}$$

where:
$F_{VAR}$ is the normalized and corrected fluorescence value,
$F_{VAR}(t)$ is the corrected fluorescence value at time t, and
$F_o$ is the estimated initial fluorescence.

20. The method as described in claim 19 further comprising:
(a) monitoring the intensity of light in the chamber at pre-determined intervals;

(b) controlling the intensity of light in the chamber so that the intensity remains within a pre-determined intensity range;

(c) monitoring the temperature in the chamber at pre-determined intervals and warning the operator if the temperature exceeds a pre-determined amount; and (d) monitoring the temperature in the filter cooling system at pre-determined intervals and warning the operator if the temperature exceeds a pre-determined amount.

21. An apparatus for determining the photosynthetic activity of a plant, comprising:

(a) a chamber having light impermeable walls, for housing a plant, said chamber having a conduit for admitting light into the chamber;

(b) illuminating means for illuminating the plant through the conduit;

(c) controlling means for controlling the intensity of the illuminating means;

(d) monitoring means, responsive to the intensity of light in the chamber and communicating with the controlling means, for monitoring the intensity of light in the chamber at predetermined time intervals and for adjusting the controlling means based on the monitored light intensity to maintain the light intensity in the chamber within a predetermined intensity range; and (e) photosynthesis measuring means connected to the chamber for measuring the photosynthetic activity of the plant induced by light from said illuminating means, comprising light intensity measuring means for measuring the light intensity in the chamber corresponding to the wavelengths of light which are characteristic of fluorescence emission from a plant;

(f) light selecting means for allowing only light of wavelengths corresponding to the wavelengths characteristics of plant fluorescence emission to pass to said light intensity measuring means.

22. An apparatus as described in claim 21 wherein said wavelength is between 460 and 625 nanometers.

23. An apparatus as described in claim 21 wherein said light selecting means is a light filter which permits only light of wavelength greater than 685 nanometers to pass to said light intensity measuring means.

24. An apparatus as described in claim 21 wherein the light intensity measuring means is a photodiode.

25. An apparatus as described in claim 21 wherein the illuminating means is a D.C. powered lamp and the controlling means a voltage regulator.

26. An apparatus as described in claim 21, further comprising light introduction means for introducing light from the illuminating means into the chamber in a virtually instantaneous manner.

27. An apparatus as described in claim 26 wherein the light introduction means is a shutter.

28. An apparatus as defined in claim 21, further comprising analyzing means for recording and analyzing signals from the photosynthesis measuring means.

29. An apparatus as defined in claim 28 wherein said analyzing means further comprises converting means for converting analog signals from the photosynthesis measuring means into digital signals for the analyzing means.

30. A method of determining the corrected and normalized fluorescence emission from a plant, comprising the steps of:

(a) measuring and storing a value for a dark signal in a chamber with no outside illuminating applied in the chamber;

(b) measuring and storing a value for straylight signal in the chamber when empty, with light illumination of a pre-determined intensity applied therein;

(c) introducing a plant sample into the chamber after the application of illumination in the chamber is discontinued;

(d) measuring and storing values for fluorescence in the chamber at pre-determined intervals upon initial application of illumination in the chamber;

(e) estimating and storing values for fluorescence of the sample in the chamber before the onset of photochemistry based on the measurement of fluorescence in the chamber on initial application of illumination;

(f) measuring and storing values for fluorescence of the sample in the chamber over a pre-determined time period at pre-determined intervals during illumination of the chamber;

(g) correcting the measured fluorescence values by eliminating the effects of the dark signal and the straylight signal; and (h) normalizing the of fluorescence values.

31. The method as described in claim 30 further comprising:

(a) monitoring the intensity of light in the chamber at pre-determined intervals;

(b) controlling the intensity of light in the chamber so that the intensity remains within a pre-determined intensity range;

(c) monitoring the temperature in the chamber at pre-determined intervals and warning the operator if the temperature exceeds a pre-determined amount; and (d) monitoring the temperature in the filter cooling system at pre-determined intervals and warning the operator if the temperature exceeds a pre-determined amount.

32. The method as described in claim 30 wherein the step of correcting the values for fluorescence is by using the formula:

$$F_{VAR}(t) = F_{meas}(t) - L_{ST} - Ds$$

where:

$F_{VAR}(t)$ is corrected fluorescence value at time t $F_{meas}(t)$ is the measured fluorescence value at time t $L_{ST}$ is the straylight signal, and Ds is the dark signal.

33. The method as described in claim 30 wherein the step of normalizing fluorescence values is by using the formula:

$$F_{VAR} = \frac{F_{VAR}(t) - Fo}{Fo}$$

where:

$F_{VAR}$ is the normalized and corrected fluorescence value, $F_{VAR}(t)$ is the corrected fluorescence value at time t, and Fo is the estimated initial fluorescence.

* * * * *